United States Patent
Königsmann et al.

(10) Patent No.: US 8,624,075 B2
(45) Date of Patent: Jan. 7, 2014

(54) ISOMERIZATION OF LINEAR ALPHA-OLEFINS

(75) Inventors: Lucia Königsmann, Stuttgart (DE);
Ekkehard Schwab, Neustadt (DE);
Thilo Hahn, Kirchheimbolanden (DE);
Germain Kons, Jersey City, NJ (US)

(73) Assignee: BASF SE (DE)

( * ) Notice: Subject to any disclaimer, the term of this patent is extended or adjusted under 35 U.S.C. 154(b) by 0 days.

(21) Appl. No.: 13/518,246

(22) PCT Filed: Dec. 20, 2010

(86) PCT No.: PCT/EP2010/070207
§ 371 (c)(1),
(2), (4) Date: Jun. 21, 2012

(87) PCT Pub. No.: WO2011/076718
PCT Pub. Date: Jun. 30, 2011

(65) Prior Publication Data
US 2012/0271090 A1    Oct. 25, 2012

(30) Foreign Application Priority Data
Dec. 22, 2009 (EP) .................................. 09180313

(51) Int. Cl.
*C07C 5/23* (2006.01)
(52) U.S. Cl.
USPC ........... 585/664; 502/215; 502/325; 502/326; 502/339; 585/670

(58) Field of Classification Search
USPC .......... 585/664, 670, 671; 502/215, 230, 235, 502/339
See application file for complete search history.

(56) References Cited

U.S. PATENT DOCUMENTS

| | | | | | |
|---|---|---|---|---|---|
| 3,919,340 | A | * | 11/1975 | Hayes | ............................ 585/668 |
| 4,310,709 | A | * | 1/1982 | Rebafka | ......................... 568/687 |
| 4,417,089 | A | | 11/1983 | Drake | |
| 5,502,269 | A | | 3/1996 | Sarrazin et al. | |
| 6,211,114 | B1 | * | 4/2001 | Brocker et al. | ............... 502/215 |
| 2010/0286458 | A1 | | 11/2010 | Iselborn et al. | |
| 2011/0112203 | A1 | | 5/2011 | Steiner et al. | |
| 2011/0112205 | A1 | | 5/2011 | Steiner et al. | |

FOREIGN PATENT DOCUMENTS

| DE | 2751766 A1 | 5/1979 |
|---|---|---|
| EP | 0636677 A1 | 2/1995 |
| EP | 0841090 A2 | 5/1998 |
| WO | WO-2008/124375 A1 | 10/2008 |
| WO | WO-2009/050194 A1 | 4/2009 |

OTHER PUBLICATIONS

U.S. Appl. No. 12/950,646.
International Search Report for PCT/EP2010/070207 mailed Feb. 24, 2011.

* cited by examiner

*Primary Examiner* — Walter D Griffin
*Assistant Examiner* — Jelitza Perez
(74) *Attorney, Agent, or Firm* — Novak Druce Connolly Bove + Quigg LLP

(57) ABSTRACT

Process for isomerizing linear alpha-olefins having from 10 to 25 carbon atoms over a heterogeneous catalyst.

13 Claims, No Drawings

ISOMERIZATION OF LINEAR ALPHA-OLEFINS

RELATED APPLICATIONS

This application is a national stage application (under 35 U.S.C. §371) of PCT/EP2010/070207, filed Dec. 20, 2010, which claims benefit of European Patent Application No. 09180313.0, filed Dec. 22, 2009.

The invention relates to a process for isomerizing linear alpha-olefins.

Linear alpha-olefins are prepared from ethylene. The terminal (=alpha) C=C double bond is subsequently rearranged "inward" to form the thermodynamically favored linear internal olefins. Such isomerized olefins are referred to as linear internal olefins (LIOs) and are valuable products for preparing ASA (alkenylsuccinic anhydride). ASA is used in the paper industry. ASA is prepared by reacting the LIOs with MAn (maleic anhydride).

Numerous processes for the double bond isomerization of olefins are known and can be carried out in a wide temperature range from below 100° C. to above 250° C. The temperature level has a critical influence on the isomer composition. Such isomerization reactions can be carried out both with and without addition of hydrogen. However, oligomerization and skeletal isomerization can occur as secondary reactions in the absence of hydrogen. The isomerization in the presence of hydrogen can hydrogenate the double bond and lead to saturated products. To carry out the isomerization economically with minimal hydrogenation of the double bond, use of a gas mixture of hydrogen and nitrogen is known, with the addition of hydrogen being kept low.

EP 0 841 090 A2 discloses a fixed-bed catalyst and a continuous process for preparing 2-buten-1-ol compounds, in which the fixed-bed catalyst comprises palladium and selenium or tellurium or a mixture of selenium and tellurium on a silicon dioxide support. WO 2008/124375 A1 discloses a process for preparing internal olefins by catalytic isomerization of alpha-olefins, in which potassium carbonate or potassium acetate on an oxide support is used as catalyst. The isomerization of olefins having from 4 to 20 carbon atoms, in particular butene, in the presence of a heterogeneous catalyst comprising nickel and at least one element of group VIB is known from WO 2009/050194 A1. U.S. Pat. No. 4,417,089 discloses the hydroisomerization of terminal olefins over a catalyst comprising essentially a palladium component, a cerium component and aluminum.

The isomerization of alpha-olefins to internal olefins using a palladium-based catalyst loaded with a sulfur component is already known from EP 0 636 676 A1 and the corresponding U.S. Pat. No. 5,569,806 and from EP 0 636 677 A1 and the corresponding U.S. Pat. No. 5,502,269.

Disadvantages of the known processes are unsatisfactorily low yields, for example as a result of secondary reactions such as branching, low selectivity and high prices of the catalysts.

It was an object of the invention to provide an improved process for the isomerization, in particular hydroisomerization, of linear alpha-olefins having from 10 to 25 carbon atoms, which makes an improved yield and selectivity possible.

The invention provides a process for isomerizing linear alpha-olefins having from 10 to 25 carbon atoms over a heterogeneous catalyst, wherein the heterogeneous catalyst comprises palladium and selenium and/or tellurium on a support.

The catalyst thus has palladium and selenium or palladium and tellurium or palladium and selenium plus tellurium as significant constituents.

Preference is given to a catalyst which comprises palladium and selenium or tellurium or a mixture of selenium and tellurium on a silicon dioxide support and has a BET surface area of from 80 to 380 $m^2/g$ and a pore volume of from 0.6 to 0.95 $cm^3/g$ in the pore diameter range from 3 nm to 300 μm, with from 80 to 95% of the pore volume being in the pore diameter range from 10 to 100 nm.

The catalyst preferably comprises from 0.1 to 2.0% by weight of palladium and from 0.01 to 0.2% by weight of selenium, tellurium or a mixture of selenium and tellurium, based on the total weight of the catalyst. In a preferred embodiment, the catalyst is doped with from 0.01 to 0.07% by weight of selenium, based on the total weight of the catalyst.

The BET surface area is preferably from 100 to 150 $m^2/g$, in particular from 110 to 130 $m^2/g$. The BET surface area is determined by $N_2$ adsorption in accordance with DIN 66131.

In particular, the catalyst comprises from 0.2 to 0.8% by weight, in particular from 0.4 to 0.6% by weight, of palladium. The catalyst preferably comprises from 0.02 to 0.08% by weight, in particular from 0.04 to 0.06% by weight, of selenium, tellurium or a mixture of selenium and tellurium, preferably selenium.

Apart from the active components mentioned, small amounts of further metals can be present on the catalyst. Preference is given to only palladium, selenium and/or tellurium, in particular only palladium and selenium, being present on the silicon dioxide support.

The catalysts to be used according to the invention can be produced by any suitable processes. They are preferably produced by impregnating a silicon dioxide support with a solution of a palladium compound and a selenium compound or tellurium compound or a mixture of a selenium compound and a tellurium compound. It is possible to use one or more palladium compounds, selenium compounds and/or tellurium compounds. The compounds are preferably used in the form of aqueous solutions. Palladium is preferably used in the form of salts such as palladium nitrate, or complexes. Selenium and/or tellurium are used, for example, in oxidic form. Further suitable palladium, selenium and tellurium compounds are described in DE-A-27 51 766. The silicon dioxide support can be impregnated in succession with solutions of the individual compounds in any order, with the catalyst support being able to be dried between the individual impregnation steps. However, the catalyst support can also be impregnated with a solution comprising the compounds of the active substances in an appropriate desired ratio. The concentration of the solutions can be selected so that the desired amount of palladium and selenium and/or tellurium can be applied to the catalyst by means of a single impregnation step. However, application by means of multiple impregnation is also possible.

The catalyst support is preferably moved in the solution of the active substances, and the impregnated catalyst is then dried at a temperature of about 120° C. and subsequently heated at a temperature of about 200° C. The active substances, i.e. palladium and selenium and/or tellurium, are reduced in the presence of hydrogen before or during use of the catalyst in the isomerization.

The catalyst support is preferably produced by precipitating silicon dioxide from an alkali metal silicate solution and drying the precipitate and pressing it to form shaped bodies, and calcining the resulting shaped bodies at a temperature in the range from 400 to 1100° C., preferably from 600 to 900° C., in particular from 800 to 900° C.

Here, for example, aqueous ammoniacal alkali metal silicate solution is placed in a reaction vessel and treated with aqueous sulfuric acid so that silicon dioxide precipitates. The precipitate obtained can then be filtered off, washed and spray dried. Spray drying is preferably carried out so that the silicon dioxide powder obtained has a water content corresponding to a loss on ignition of from 25 to 35% by weight on ignition at 900° C. for 2 hours. The silicon dioxide powder obtained can then be converted into a paste using a peptizing agent and brought to the desired shape. When the catalyst is used as fixed-bed catalyst, it can have all suitable macroscopic shapes, for example in the form of extrudates, tablets, pellets of any shape, spheres or rings. The silicon dioxide powder is preferably pressed to form extrudates. The extrudates are then dried at from 120 to 150° C. and subsequently calcined at from 400 to 1100° C., preferably from 600 to 900° C., in particular from 800 to 900° C.

Other production processes for the silicon dioxide support can be chosen as long as the supports obtained have the indicated BET surface area, pore size and pore size distribution.

In a particularly preferred embodiment, the catalyst is used as fixed-bed catalyst.

Reactor

The isomerization of the invention can be carried out in any desired apparatus in which a continuous process is possible. The isomerization is preferably carried out in the downflow mode in a tube reactor comprising the fixed-bed catalyst to be used according to the invention. The tube reactor then preferably comprises a gas distributor, for example in the form of a filter plate, a static mixer or a nozzle, in the upper part. The gas distributor serves for introducing gas mixture (hydrogen/nitrogen) so that the reactor cross section is preferably uniformly supplied with gas. The compound to be isomerized is firstly passed through a heating zone, mixed with the gas and fed into the reactor. The space velocity over the catalyst is set so that a conversion of preferably from 70 to 99%, particularly preferably from 90 to 99%, is achieved at the reactor outlet. The supply of hydrogen is set as a function of temperature and total pressure so that a hydrogen partial pressure of from 0.1 to 5 bar, preferably from 0.1 to 2 bar, in particular from 0.1 to 1 bar, is maintained. The hydrogen passed through can, after condensation of low boilers from the reactor outlet, be discharged as offgas or be recirculated to the process.

Process Parameters

The isomerization is preferably carried out at a pressure of from 0.5 to 5 bar absolute, in particular from 0.8 to 2 bar absolute.

The isomerization is carried out at temperatures in the range from 80 to 150° C., preferably from 120° C. to 140° C. In another preferred embodiment, the isomerization is carried out at from 100 to 120° C. Here, depending on the starting compound used, the isomerization is operated at space velocities over the catalyst of from 0.5 to 5 l/l (catalyst)×h, preferably from 1 to 3 l/l (catalyst)×h.

In a preferred embodiment, the isomerization is carried out in the presence of hydrogen or a mixture of hydrogen and inert gas, preferably nitrogen. In a very particularly preferred embodiment, the inert gas used in the isomerization is nitrogen, with the hydrogen used being used in an amount of from 5 to 50 mmol % based on nitrogen.

The process of the invention can be carried out in the presence or absence of an inert organic solvent. Inert organic solvents which can be used are, for example, ethers such as diethyl ether, dioxane, tetrahydrofuran, alcohols such as ethanol, isobutanol, aromatic or aliphatic hydrocarbons such as heptane or benzene or mixtures thereof. Preference is given to working without an inert organic solvent.

Starting Materials

The linear alpha-olefins to be isomerized can be present as uniform compounds or as a mixture of hydrocarbons having different chain lengths. Examples of commercially available linear alpha-olefins are C16-C18-olefins. In a preferred embodiment, the linear alpha-olefin is a monoolefin. Particular preference is given to the linear alpha-olefin having the empirical formula $C_{18}H_{36}$.

In the isomerization of the invention, the double bond is preferably shifted to the 2 position. Preferred products in the isomerization of 1-octadecene are 2-octadecene and also 3-octadecene and 4-octadecene.

The olefins which have been isomerized according to the invention are particularly suitable for preparing ASA (alkenylsuccinic anhydride).

In a preferred embodiment, the process of the invention for isomerizing olefins having from 10 to 25 carbon atoms is carried out in the absence of lower homologues, in particular in the absence of butenes.

EXAMPLES

Catalyst Production

An aqueous ammoniacal sodium silicate solution was placed in a stirred vessel. Silicon dioxide was precipitated by means of aqueous sulfuric acid while stirring. The precipitate obtained was filtered off, washed and subsequently spray dried. Spray drying was carried out so that the silicon dioxide powder obtained has a water content corresponding to a loss on ignition in the range from 25 to 35% by weight in 2 hours at 900° C. The silicon dioxide powder obtained in this way was made into a paste using water and ammonia as peptizing agent and pressed to form extrudates having a diameter of 3 mm. The extrudates were dried at from 120 to 150° C. in a drying oven and subsequently calcined at from 820 to 870° C.

300 g of the support material obtained in this way in the form of extrudates having a diameter of 3 mm were admixed with an aqueous solution of 13.64 g of palladium nitrate solution comprising 11% by weight of palladium and 0.21 g of $SeO_2$ in 244 g of distilled water in a round-bottomed flask on a rotary evaporator. The flask was rotated at room temperature until the entire solution had been absorbed by the support material. The flask together with the catalyst was subsequently heated to 120° C. while being rotated and dried at a rotation rate of 9 revolutions per minute while introducing 2000 l of air per hour over 3 hours. After drying, the temperature was increased to 200° C. while continually rotating the flask and introducing 1000 l of air/h and the catalyst was heated for 3 hours.

The silicon dioxide supported catalyst obtained in this way comprised 0.5% by weight of palladium and 0.05% by weight of selenium, based on the total weight of the catalyst. The BET surface area is 119 m$^2$/g and the pore volume is 0.82 cm$^3$/g in the pore diameter range from 3 nm to 300 µm. Of this pore volume, 91.7% was in the pore diameter range from 10 nm to 100 nm.

Reactor

The reactor used was a double-walled glass reactor having an internal diameter of 6 mm and a length of 124 cm. It was filled with the catalyst indicated above and flushed with 5 l/h of nitrogen. The catalyst was subsequently activated by reduction at 150° C. in 20 l/h of hydrogen for one hour.

EXAMPLES

The reactor filled with the catalyst to be used according to the invention was started under the following conditions:

Example 1

Feed stream of
20 g/h of 1-octadecene
2.5 l/h of hydrogen (H$_2$) and
3.5 l/h of nitrogen (N$_2$)
Temperature: 140° C.
Running time: 6 days
Space velocity over the catalyst: 2.2 g/ml×h The reactor was operated in the upflow mode at atmospheric pressure over the entire running time. A conversion of >98% and a selectivity of 90% were achieved.

Example 2

Feed stream of
20 g/h of 1-octadecene
2.5 l/h of hydrogen (H$_2$) and
3.5 l/h of nitrogen (N$_2$)
Temperature: 140° C.
Running time: 5 days
Space velocity over the catalyst: 2.2 g/ml×h The reactor was operated in the downflow mode at atmospheric pressure over the entire running time. A conversion of 93% and a selectivity of 89% were achieved.

Example 3

Feed stream of
50 g/h of 1-octadecene
0.1-0.3 l/h of hydrogen (H$_2$) and
2.9 l/h of nitrogen (N$_2$)
Temperature: 115-140° C.
Running time: 14 days The reactor was operated in the downflow mode at atmospheric pressure and a space velocity over the catalyst of 3.6 g/ml×h over the entire running time. A conversion of 70% at a selectivity of >99% was achieved.

The following product distribution was obtained:

TABLE 1

| | Product distribution | | | | | | |
|---|---|---|---|---|---|---|---|
| Examples | 1-Octadecene % by wt | 2-Octadecene % by wt | 3-Octadecene % by wt | 4+-Octadecene % by wt | Octadecane % by wt | Conversion % | Selectivity to LIOs % |
| Example 1 | 1.4 | 37.1 | 19.4 | 32.4 | 9.7 | 98.6 | 89.9 |
| Example 2 | 6.9 | 44.8 | 15.3 | 23.1 | 9.9 | 93.08 | 89.4 |
| Example 3 | 29.8 | 52.5 | 7.9 | 9.6 | 0.2 | 69.5 | 99.7 |

It can be seen from the values reported above that the catalyst to be used according to the invention in conjunction with the mode of operation selected has a very good property profile, especially in respect of the selectivity to the desired LIOs.

The invention claimed is:

1. A process for isomerizing linear alpha-olefins having from 10 to 25 carbon atoms over a heterogeneous catalyst, wherein the heterogeneous catalyst comprises palladium and selenium and/or tellurium on a support.

2. The process according to claim 1, wherein the support comprises essentially silicon dioxide.

3. The process according to claim 1, wherein a catalyst which comprises palladium and selenium or tellurium or palladium and a mixture of selenium and tellurium on a silicon dioxide support and has a BET surface area of from 80 to 380 m2/g, a pore volume of from 0.6 to 0.95 cm3/g and a pore diameter of from 3 nm to 300 µm, with from 80 to 95% of the pore volume being in the pore diameter range from 10 to 100 nm, is used.

4. The process according to claim 1, wherein the catalyst comprises from 0.1 to 2.0% by weight of palladium and from 0.01 to 0.2% by weight of selenium, tellurium or a mixture of selenium and tellurium, based on the total weight of the catalyst.

5. The process according to claim 1, wherein the catalyst has a BET surface area of from 100 to 150 m$^2$/g.

6. The process according to claim 1, wherein the catalyst comprises 0.01-0.07% by weight of Se, based on the total weight of the catalyst.

7. The process according to claim 1, wherein the alpha-olefin is an olefin having from 16 to 18 carbon atoms.

8. The process according to claim 1, wherein the linear alpha-olefin is a monoolefin.

9. The process according to claim 1, wherein the isomerization is carried out at a temperature of from 100 to 120° C.

10. The process according to claim 1, wherein the isomerization is carried out at a pressure of from 0.5 to 5 bar absolute.

11. The process according to claim 1, wherein the isomerization is carried out in the presence of hydrogen or a mixture of hydrogen and inert gas.

12. The process according to claim 11, wherein the inert gas used in the isomerization is nitrogen (N2).

13. The process according to claim 1, wherein the isomerization is carried out over a fixed-bed catalyst.

* * * * *